United States Patent
Hand et al.

(10) Patent No.: US 6,582,456 B1
(45) Date of Patent: Jun. 24, 2003

(54) HEATED PATIENT SUPPORT APPARATUS

(75) Inventors: Barry D. Hand, Mt. Pleasant, SC (US); Richard L. Borders, Cincinnati, OH (US); Richard H. Heimbrock, Cincinnati, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/701,499

(22) Filed: Nov. 29, 2000

Related U.S. Application Data

(63) Continuation-in-part of application No. 09/187,989, filed on Nov. 6, 1998, now Pat. No. 6,149,674, and a continuation-in-part of application No. 09/188,785, filed on Nov. 6, 1998, now Pat. No. 6,073,284.
(60) Provisional application No. 60/090,847, filed on Jun. 26, 1998, and provisional application No. 60/127,992, filed on Apr. 6, 1999.

(51) Int. Cl.⁷ .................................................. A61F 7/00
(52) U.S. Cl. ........................ 607/108; 607/96; 219/212; 219/217; 219/544
(58) Field of Search ............................ 607/108, 96, 98, 607/99, 109, 110; 219/212, 217, 528, 544, 552

(56) References Cited

U.S. PATENT DOCUMENTS

| | | |
|---|---|---|
| 750,179 A | 1/1904 | Foglesong |
| RE22,763 E | 6/1946 | Clark |
| 2,606,996 A | 8/1952 | Westerberg et al. |
| 3,808,403 A | 4/1974 | Kanaya et al. |
| 3,854,156 A | 12/1974 | Williams |
| 4,265,789 A | 5/1981 | Christopherson et al. |
| 4,423,308 A * | 12/1983 | Callaway et al. ........... 219/217 |
| 4,668,857 A | 5/1987 | Smuckler |
| 4,857,384 A | 8/1989 | Mio et al. |
| 5,051,673 A | 9/1991 | Goodwin |
| 5,251,347 A | 10/1993 | Hopper et al. |
| 5,300,101 A | 4/1994 | Augustine et al. |
| 5,324,320 A | 6/1994 | Augustine et al. |
| 5,336,250 A | 8/1994 | Augustine |
| 5,350,417 A | 9/1994 | Augustine |
| 5,373,595 A | 12/1994 | Johnson et al. |
| 5,402,542 A | 4/1995 | Viard |
| 5,415,934 A | 5/1995 | Mori |
| 5,444,878 A | 8/1995 | Kang |
| 5,542,136 A | 8/1996 | Tappel |
| 5,647,079 A * | 7/1997 | Hakamium et al. ............ 5/713 |
| 5,683,441 A | 11/1997 | Dickerhoff et al. |
| 5,773,275 A | 6/1998 | Anderson et al. |
| 5,948,303 A * | 9/1999 | Larson ....................... 219/486 |
| 5,970,550 A | 10/1999 | Gazes |
| 6,010,528 A | 1/2000 | Augustine et al. |
| 6,033,432 A | 3/2000 | Augustine et al. |
| 6,036,722 A | 3/2000 | Augustine |
| 6,049,927 A | 4/2000 | Thomas et al. |
| 6,073,284 A * | 6/2000 | Borders .................. 607/104 X |
| 6,078,026 A * | 6/2000 | West ....................... 219/528 X |
| 6,128,796 A * | 10/2000 | McCormick et al. .......... 5/626 |
| 6,138,676 A | 10/2000 | Bruhn |
| 6,156,058 A | 12/2000 | Kappel et al. |
| 6,182,315 B1 * | 2/2001 | Lee ............................... 5/690 |

OTHER PUBLICATIONS

Gorix Electro–conductive Textiles, http://www.gorix.com/gorix/GORIX.HTM (accessed Jun. 24, 1999).
Heated Beds, http://www.gorix.com/gorix/BEDS.HTM (accessed Jun. 24, 1999).
Electro–conductive Textiles??, http://www.gorix.com/gorix/WHATARE.HTM (accessed Jun. 24, 1999).

\* cited by examiner

Primary Examiner—Kevin Lee
(74) Attorney, Agent, or Firm—Bose McKinney & Evans LLP

(57) ABSTRACT

An apparatus for warming a patient includes a patient support surface having an outer cover configured to contact the patient, an electrically conductive fabric located within the cover, and a controller electrically coupled to the conductive fabric to heat the electrically conductive fabric to a selected level.

53 Claims, 13 Drawing Sheets

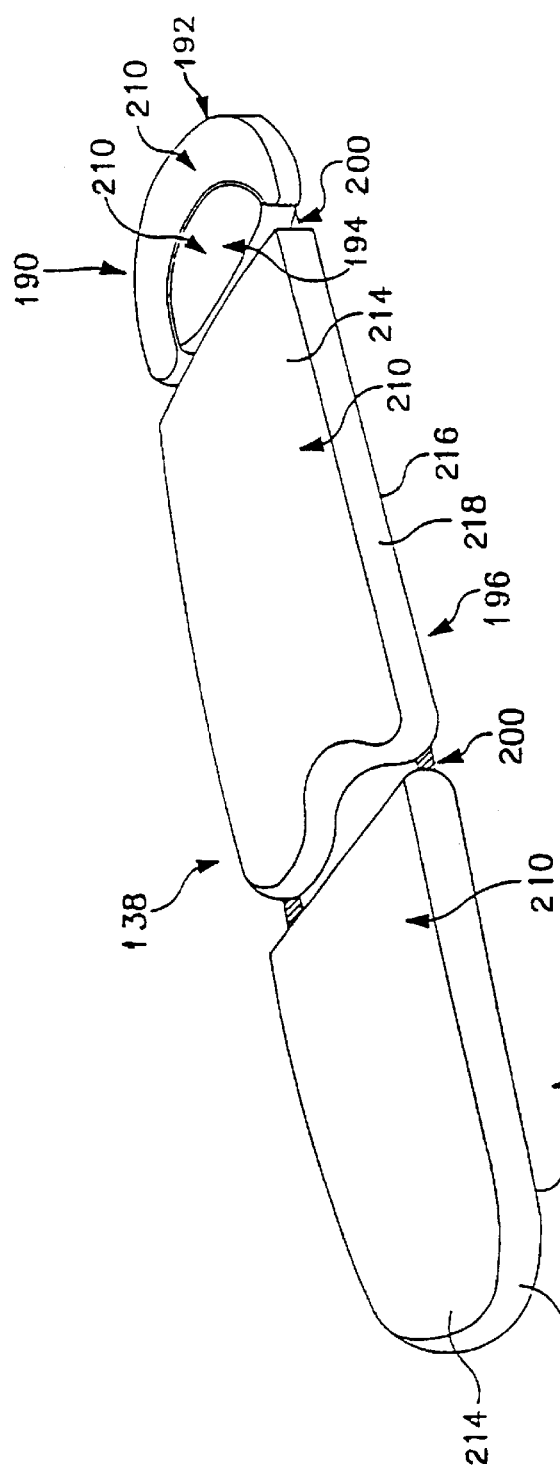
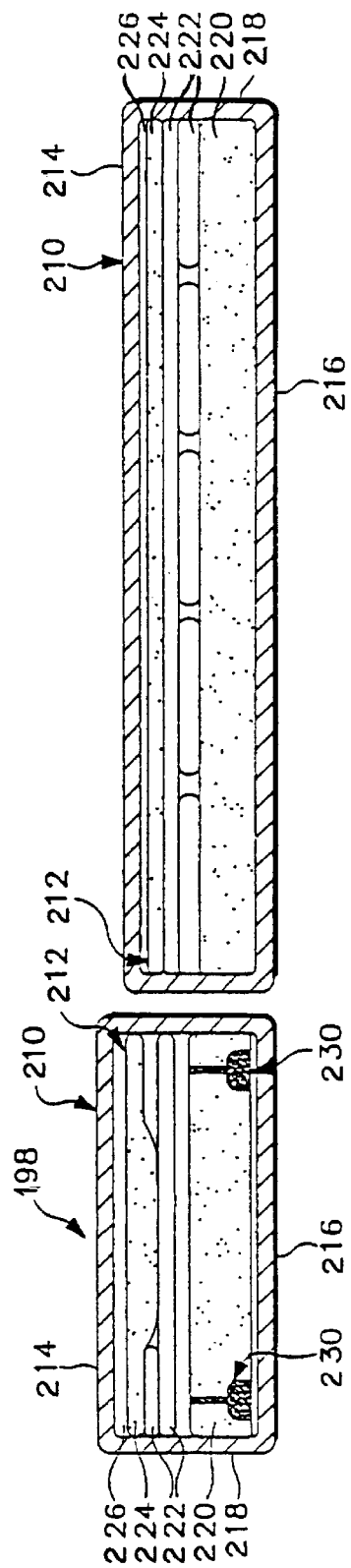

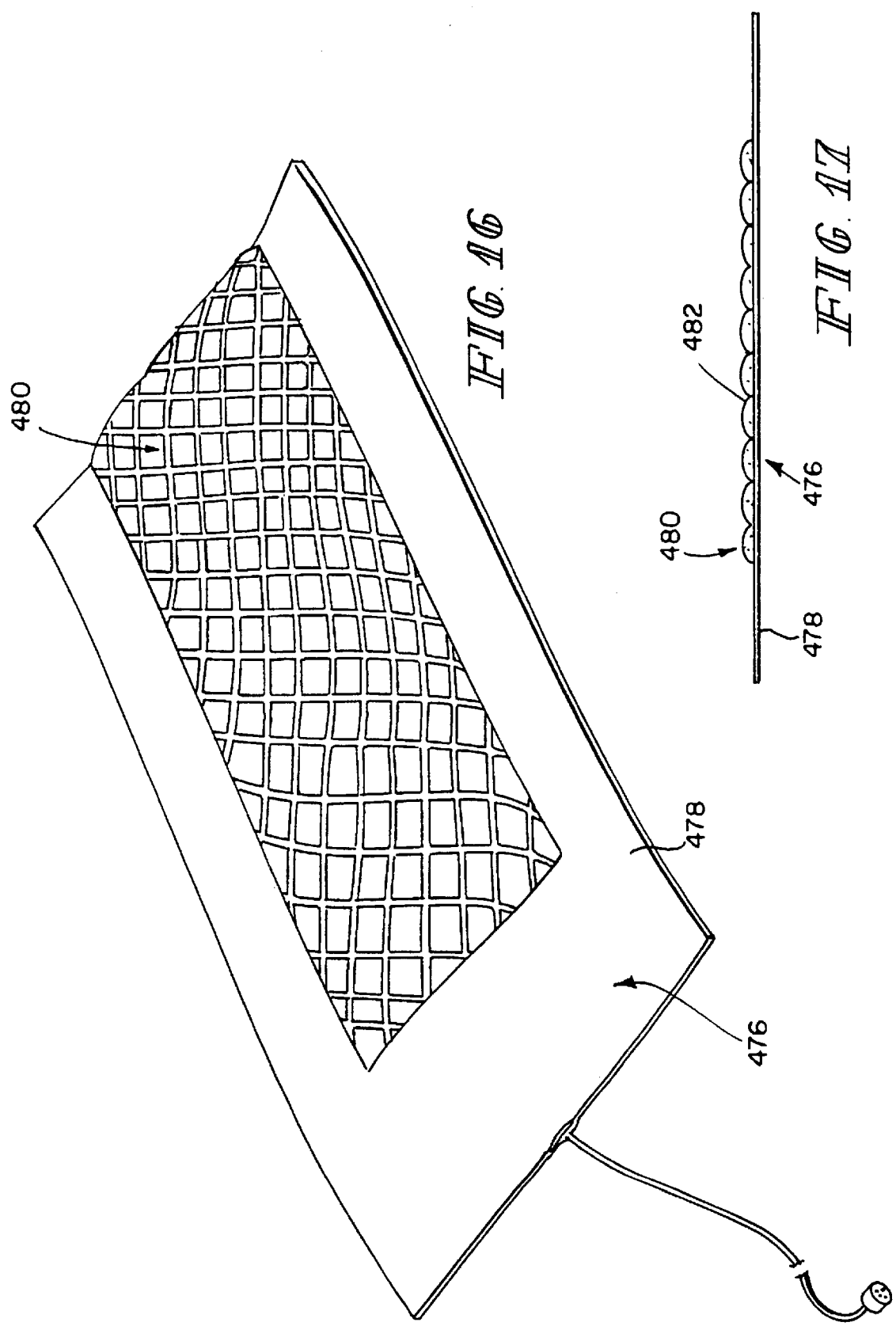

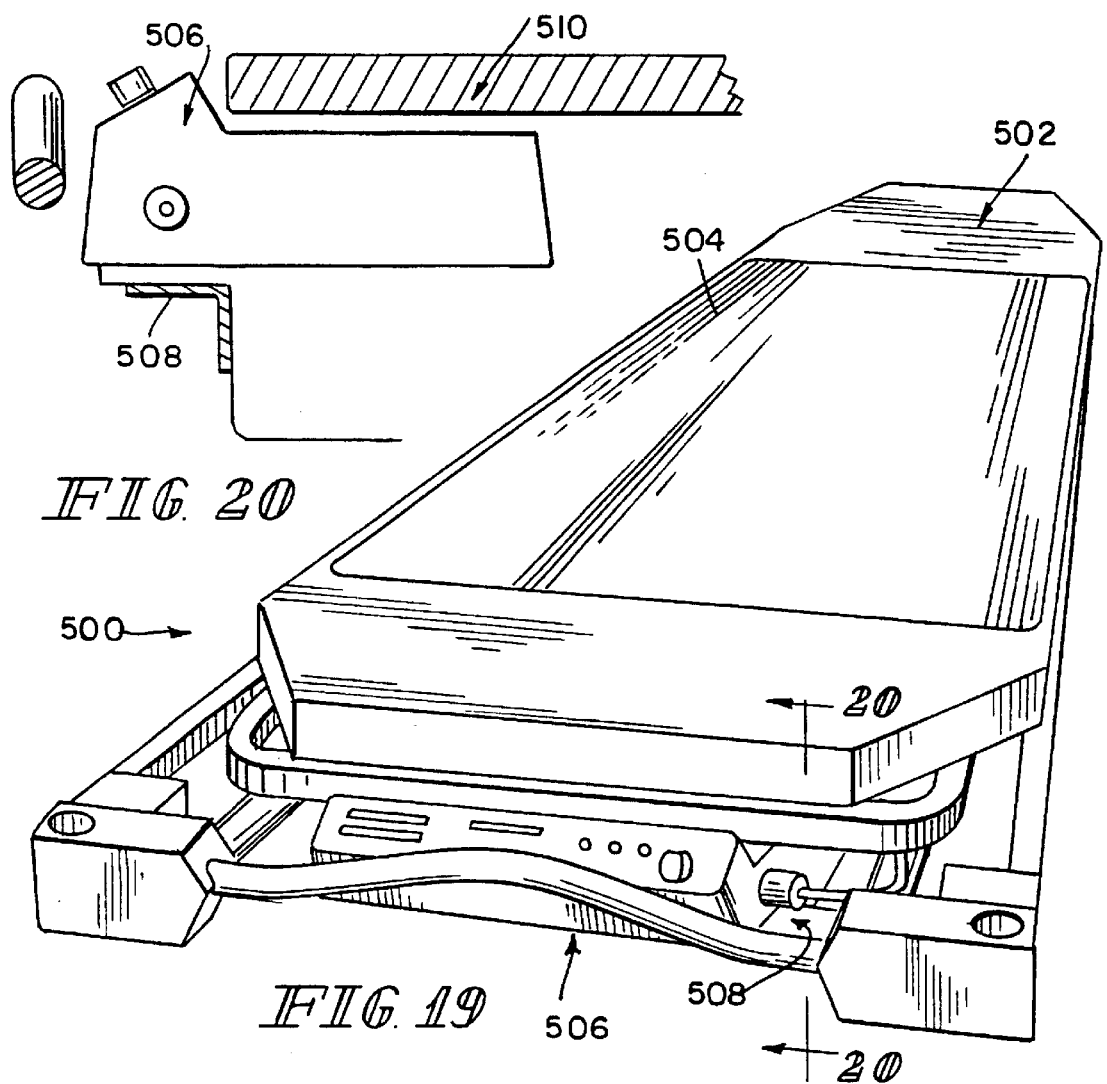
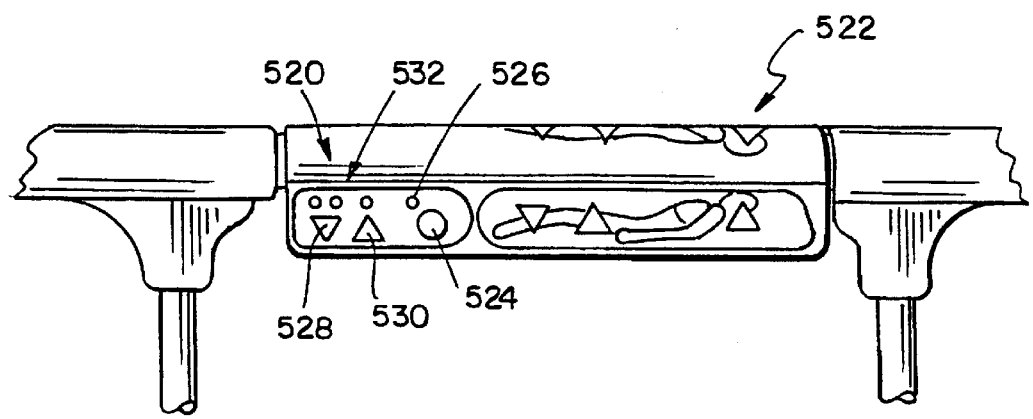

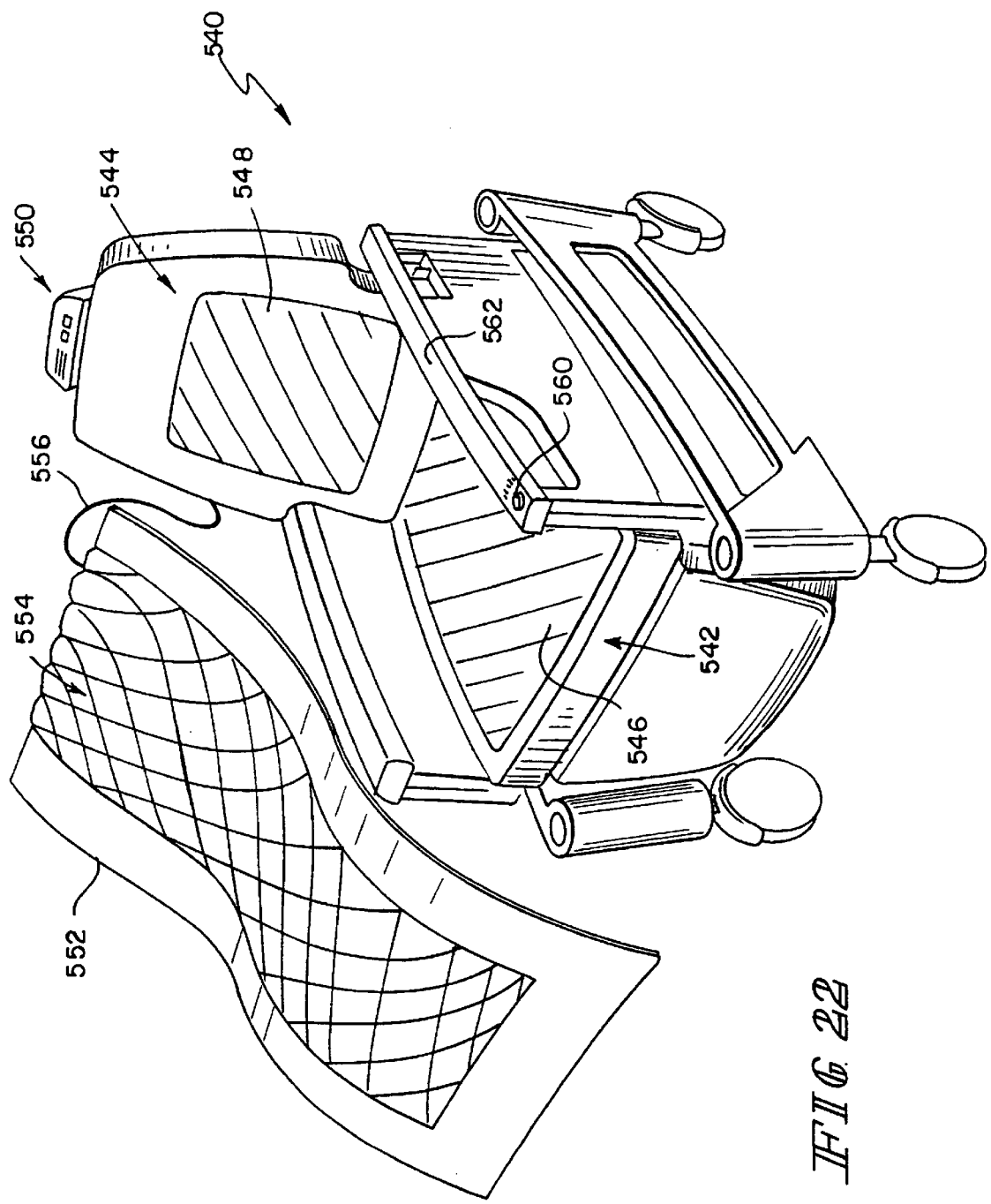

HEATED PATIENT SUPPORT APPARATUS

This application is a continuation-in-part of application Ser. No. 09/187,989, filed Nov. 6, 1998, now U.S. Pat. No. 6,149,674; a continuation-in-part of application Ser. No. 09/188,785, filed Nov. 6, 1998; now U.S. Pat. No. 6,073,284; claims the benefit of U.S. Provisional Application No. 60/090,847 filed Jun. 26, 1998; and claims the benefit of U.S. Provisional Application No. 60/127,992, filed Apr. 6, 1999.

BACKGROUND AND SUMMARY OF THE INVENTION

The present invention relates to a heated patient support apparatus. More particularly, the present invention relates to a patient support apparatus or other therapy device which includes an improved heating element to provide uniform controlled temperature regulation of the patient.

An important aspect of patient care is body temperature regulation. When a patient's body temperature remains at a constant normal state, the patient recovers faster and feels more satisfied with their stay in a hospital. A large number of patients that enter an emergency room, for instance, feel cold or hyperthermic (lowered body core temperature) and need to be warmed. Patients exiting surgery or in a recovery room are often cold due to the lower temperatures present in an operating room. Patients are transported within the emergency room and into and out of surgery on stretchers or procedural chairs.

There are two conventional heating devices used to warm patients. One device is a liquid filled pad placed under the patient. The second device is a warm air filled pad placed over the patient. Both those conventional devices are cumbersome to use and have control machines that must accompany them. These devices are not battery operated and cannot keep the patient warm during transport.

The present invention uses an improved electro-conductive textile fabric material which provides a resistive heating element. Illustratively, the material used for the heating element in the present invention is Gorix material available from Gorix LTD located in Birkdale, Southport England. It is understood that other equivalent electro-conductive textile materials may be used. The electro-conductive textile material is a polymeric substance in fiber form which is baked at a low temperature to provide a conductive material. This conductive material is coupled to a backing.

When a low voltage of 12V–24V is applied to the material, current flows through the fabric and the fabric is heated due to its resistance. The material is thin and flexible, uses a low voltage and heats very evenly. The temperature can be controlled within a range of +/−5° F. The fabric is illustratively bonded to a wipeable cover to form a heating surface of a patient support or other therapy device or a blanket. The material can be wiped down and placed under or over the patient or both.

The present invention also provides a controller for both the heated surface of a patient support and a blanket so that both the top and bottom of the patient can be warmed. For comfort warming, only one pad is used under or over the patient. For hypothermia treatment, two pads are used. The pads plug into a controller that regulates the heat output of the pads. A set point is entered for the pads and the pads are warmed to that set point and are maintained at the set point temperature. The temperature is measured by a thermostat on the pad where it will contact the skin to ensure that the patient is getting the desired heat. An alarm is provided to indicate overt temperature malfunction and battery charge warning. The controller is illustratively AC powered with a DC backup. One illustrated controller is portable and can be placed on an IV pole or siderail of the bed. Warming can continue during transport due to the battery backup feature.

Additional features of the invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying drawings in which:

FIG. 6 is a perspective view of the mattress of FIGS. 4 and 5 showing the mattress including a leg section, a torso section, and a head section;

FIG. 7 is a side sectional view of the torso section of the mattress of FIG. 6 showing the mattress having a lower foam mattress structure, high amplitude air bladders positioned atop the foam mattress structure, a Styrofoam bead bag position stabilizer positioned atop the high amplitude air bladders, and a thermal pad positioned atop the Styrofoam bead bag position stabilizer;

FIG. 8 is an end sectional view of the torso section of the mattress of FIG. 6 showing the foam mattress structure being formed to include a pair of flow paths to allow a medium to be supplied from a bottom surface of the mattress through the flow paths in the foam mattress structure so that the air bladders can be inflated and/or deflated:

FIG. 15 is a perspective view of a quilted warming blanket of the present invention;

FIG. 16 is a perspective view of another embodiment of a warming blanket of the present invention;

FIG. 17 is a sectional view taken through the warming blanket of FIG. 16;

FIG. 19 is a perspective view of a heated patient support surface and a control box integrated into a frame of a stretcher;

FIG. 20 is a sectional view taken along lines 20—20 of FIG. 19 illustrating further details of the control box;

FIG. 21 is a side view illustrating patient controls for heating integrated with a siderail of a bed or stretcher; and FIG. 22 is a perspective view of a procedural recliner including first and second warming zones on the seat and back sections of the recliner and an auxiliary blanket configured to be located over the patient.

DETAILED DESCRIPTION OF THE DRAWINGS

Figure 1:
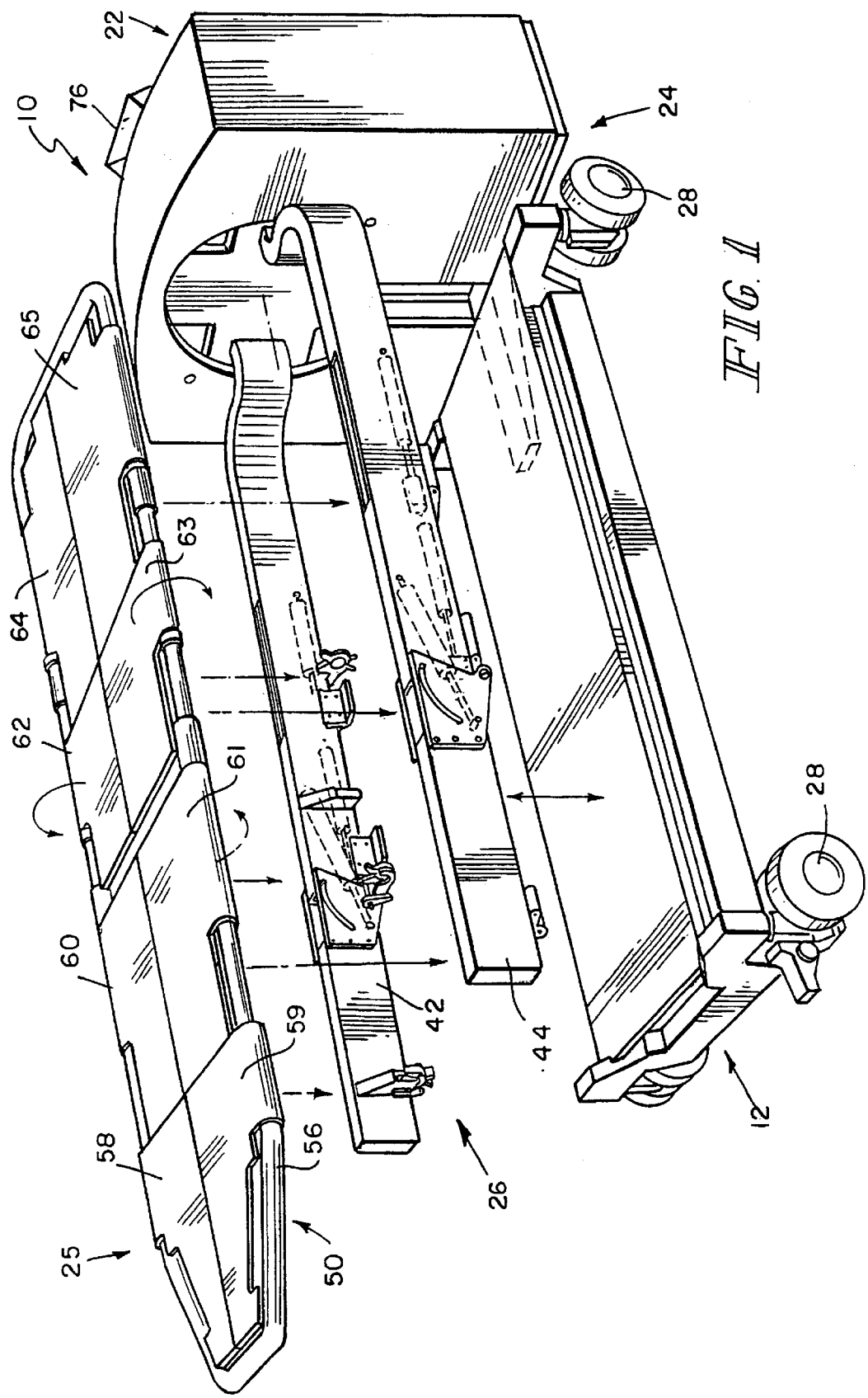
FIG. 1 is an exploded perspective view of a proning bed of the present invention including a patient support surface spaced apart from first and second support arms which are coupled to a rotating support assembly.

Referring now to the drawings, FIG. 1 illustrates a bed 10 having a base 12. A support assembly 22 is located at a foot end 24 of bed 10. Support assembly 22 illustratively supports a patient support assembly 26 in a cantilevered fashion. Therefore, the head end 25 of bed 10 is open to facilitate access to the patient (not shown). It is understood that in another embodiment of the present invention a support is coupled to the head end of the base 12 for supporting the head end of the patient support assembly 26. Therefore, the present invention is not limited to a cantilevered design. Support assembly 22 is coupled to base 12. Base 12 is supported by casters 28 which are illustratively lockable. Support assembly 22 can rotate the patient support assembly 26 about its longitudinal axis in either direction a full 360°. The present invention permits full 180° rotation of a patient located on a patient support surface while providing spinal stability for spinal trauma patients. A proning surface (not shown) is attached to the patient support assembly 26 before the patient support assembly 26 is rotated. Further details of the proning bed 10 are described in PCT International Publication No. WO 99/07320 and in PCT International Publication No. WP 99/14525, filed Jun. 25, 1999, entitled PRONING BED which are both incorporated herein by reference.

Patient support assembly 26 includes a pair of horizontally extending support arms 42 and 44 the support assembly 22. In the illustrated embodiment, the arms 42 and 44 extend away from support assembly 22 in a cantilevered fashion. A patient support surface 50 is coupled between arms 42 and 44 as discussed below.

Patient support surface 50 includes an outer frame 56 and the plurality of panels 58–65 which are pivotably coupled to the outer support frame 56 by pivot connections. In the illustrated embodiment, the panels 58–65 are all pivotable upwardly or downwardly about opposite sides of outer frame 56. This pivotable movement of panels 58–65 provides access to the patient when in the prone position.

Figure 2:
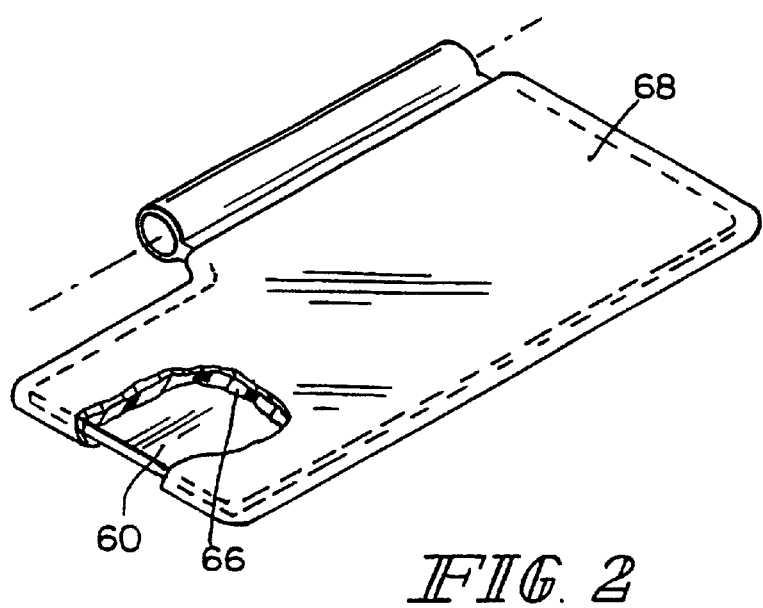
FIGS. 2 and 3 illustrate cushions configured to be located over the panels of the patient support surface, the cushions including a resistive heating element of the present invention therein.
Figure 3:
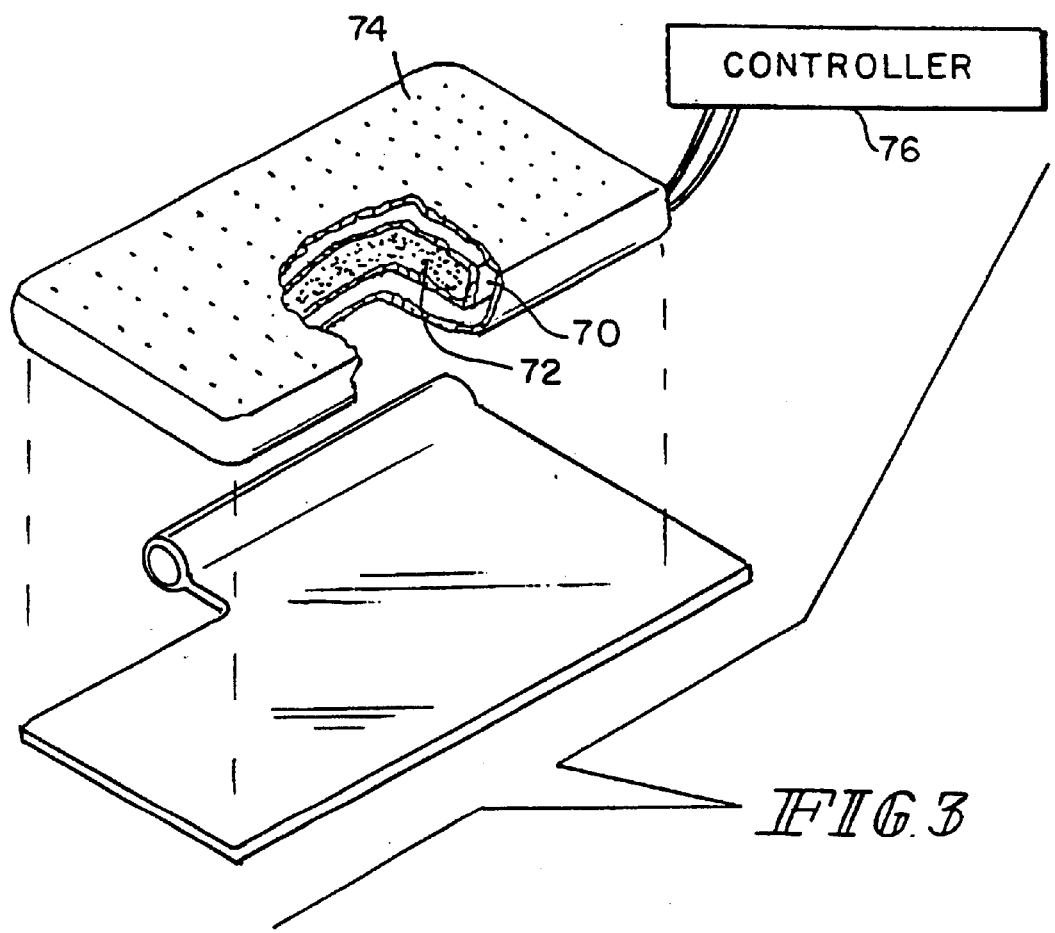

Each of the panels 58–65 of patient support surface 50 is covered with a pressure reducing surface such as foam 66, etc., and a cover 68 as shown in FIG. 2. FIG. 3 illustrates an elastic material 70 such as Spandex which is filled with styrofoam beads 72 or other material. This elastic material 70 is illustratively placed within an outer cover 74 which has a controlled air leakage and which holds its shape for a predetermined amount of time. The outer cover 74 permits the inner elastic bag 70 of styrofoam beads 72 to be conformed to the shape of the patient. In one embodiment, the outer cover 74 or the inner bag 70 is be formed to include a heating element made from, for instance, a resistive heating element such as Gorix™ material. A controller 76 is electrically coupled to the heating element. The heating material is used to warm the patient on the patient support surface 50. The beads 72 may be replaced by a phase change material embedded into the fabric or into a foam layer to extend the heat holding capability to a few hours. Such phase change material is available from Frisby.

Figure 4:
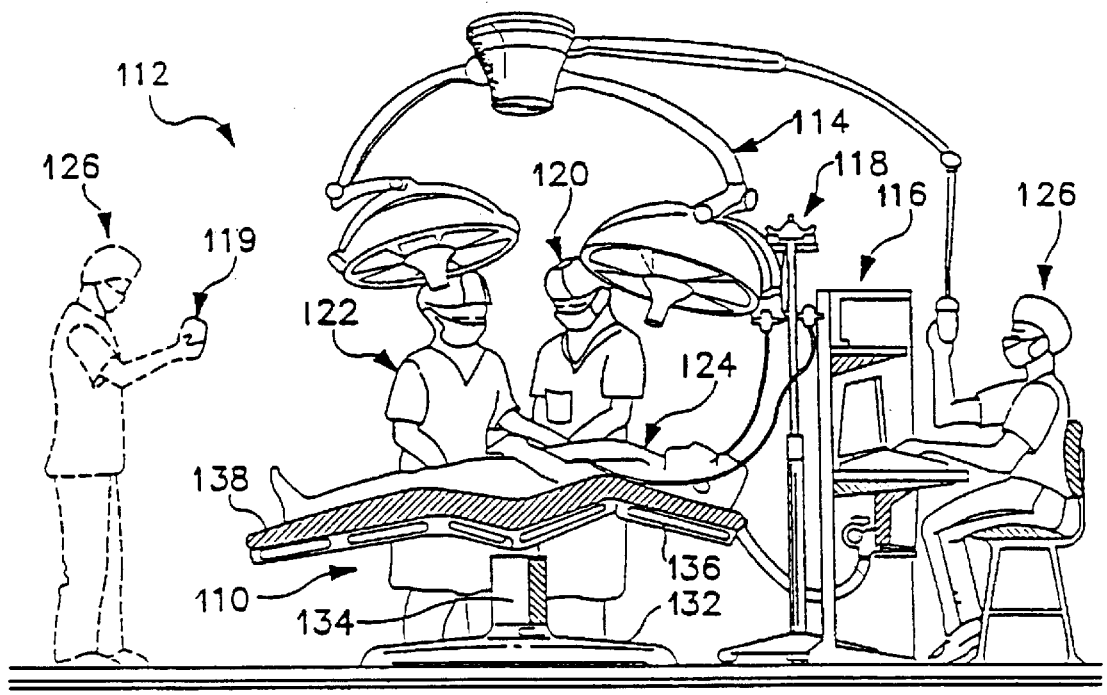
FIG. 4 is a perspective view of a surgical table of the present invention being used in an operating room environment showing a patient lying on the surgical table, a pair of surgeons operating on the patient, a first nurse sitting at a central control station configured to control the lighting, the surgical table, and other operating room equipment, and a second nurse (shown in phantom) holding a remote controller.

In another embodiment of the present invention, a surgical table 110 is shown in FIG. 4 as it would normally appear in an operating room 112. As shown in FIG. 1, operating room 112 includes surgical table 110, a surgical lighting system 114, a control station 116, an IV stand 118, and a medical device controller 119. As shown in FIG. 4, a surgeon 120 and one or more assistants 122 typically perform a procedure on a patient 124 while another caregiver 126, such as an anesthesiologist or a nurse, controls and monitors operating room equipment, including surgical table 110, from control station 116 or from a remote location using controller 119 (as shown in phantom).

Figure 5:
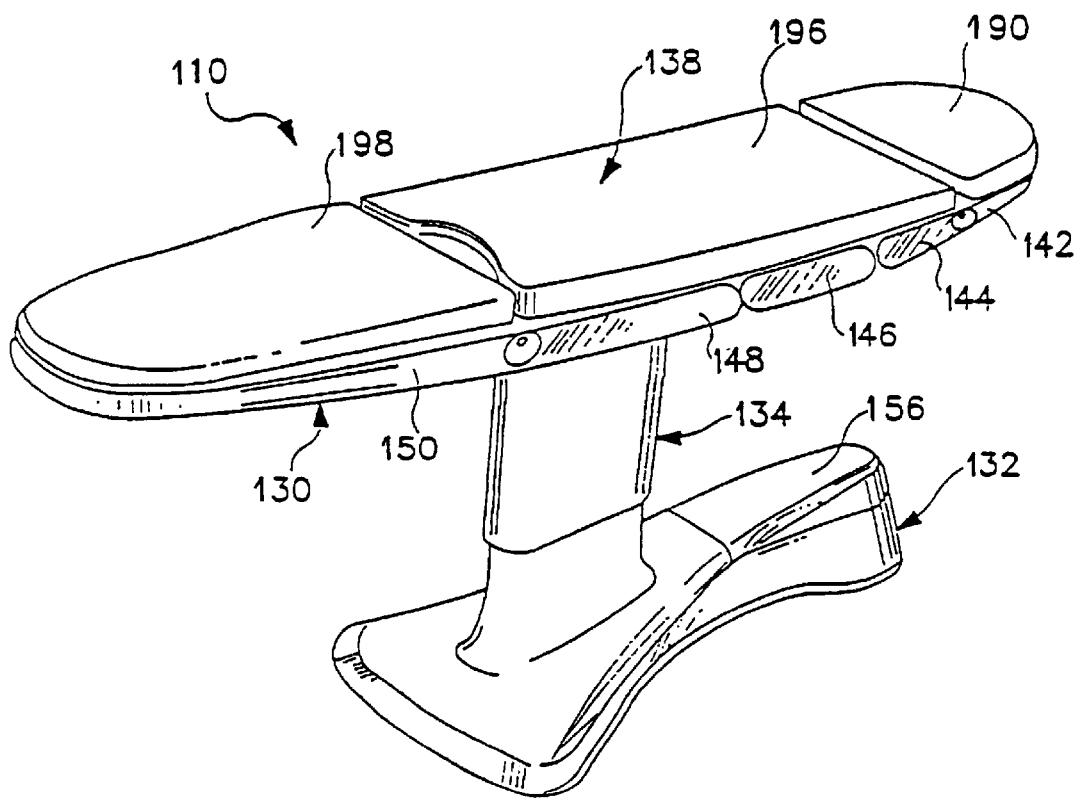
FIG. 5 is a perspective view of the surgical table of FIG. 4 showing the surgical table including a base, a vertical support member (or pedestal) extending upwardly from the base, and an articulated frame extending outwardly from the support member and showing a mattress positioned to lie on the frame and configured to support a patient during a surgical procedure.

As shown in FIGS. 4 and 5, table 110 includes articulated frame 130, base 132, a pedestal 134 interconnecting articulated frame 130 and base 132, and a mattress 138 positioned atop articulated frame 130. Articulated frame 130 includes a head section 142, an upper back section 144, a lower back section 146, a seat section 148, and at least one leg section 150, as shown in FIG. 5. Sections of frame 130 are coupled to longitudinally adjacent sections via pivots so that adjacent sections can be rotated with respect to each other by motors (not shown). Thus, table 110 is configured to receive control signals from control station 116 and/or controller 119 to move sections of articulated frame 130 so that patient 124 can be positioned in a predetermined surgical position as shown in FIG. 1.

Mattress 138 is shown in more detail in FIG. 6. Mattress 138 includes a head section 190, a torso section 196, and a leg section 198. The head section 190 of mattress 138 may also include an outer head section 192 and an inner head section 194. Each section is coupled to its adjacent section using a connector 200 to allow the medium supplied by control apparatus 186 to be transmitted to the appropriate section of mattress 138.

Each section of mattress 138 includes an outer cover 210 defining an interior region 212 of the respective section. The outer cover 210 of each section of mattress 138 includes a top surface 214, a bottom surface 216, and a perimeter surface 218 interconnecting the top and bottom surfaces 214, 216. The top surface 214 of outer cover 210 is configured to provide a patient-support platform for receiving patient 124. The bottom surface 216 of outer cover 210 is configured to lie on frame 130.

Each portion of mattress 138 also includes a foam mattress structure 220, a plurality of air bladders 222, a bead bag position stabilizer 224, and a thermal pad 226 configured to lie within the interior region 212 of the respective section of mattress 138. As shown in FIG. 7, foam mattress structure 220 is formed to include a pair of flow paths 230 to allow the medium supplied by control apparatus 186 to pass through foam mattress structure 220 to air bladders 222. Illustratively, foam mattress structure 220 is made from a Styrofoam material, although a wide variety of different materials may also be used.

Thermal pad 226 is positioned above air bladders 222 so that thermal pad 226 is positioned adjacent to top surface 214 of outer cover 210. Thermal pad 226 is configured to provide heat to patient 124 lying on top of mattress 138. Thermal pad 226 can be any type of heating device that provides heat to patient 124. Illustratively, thermal pad 226 is made from a conductive thermal material (such as Gorix™) which provides uniform heat across the material when low-voltage electricity is supplied to the material.

The temperature of mattress 138 is adjusted using controller 116, 119, and/or 219 so that control apparatus 186 supplies the necessary signal to thermal pad 226 to change the temperature of thermal pad 226. For example, when thermal pad 226 is a conductive material (such as Gorix™), control apparatus 186 supplies a voltage signal to thermal pad 226 to change the temperature of thermal pad 226. Further details of the surgical table 10 are described in PCT International Publication No. WO 99/23992 which is incorporated herein by reference.

Figure 9:
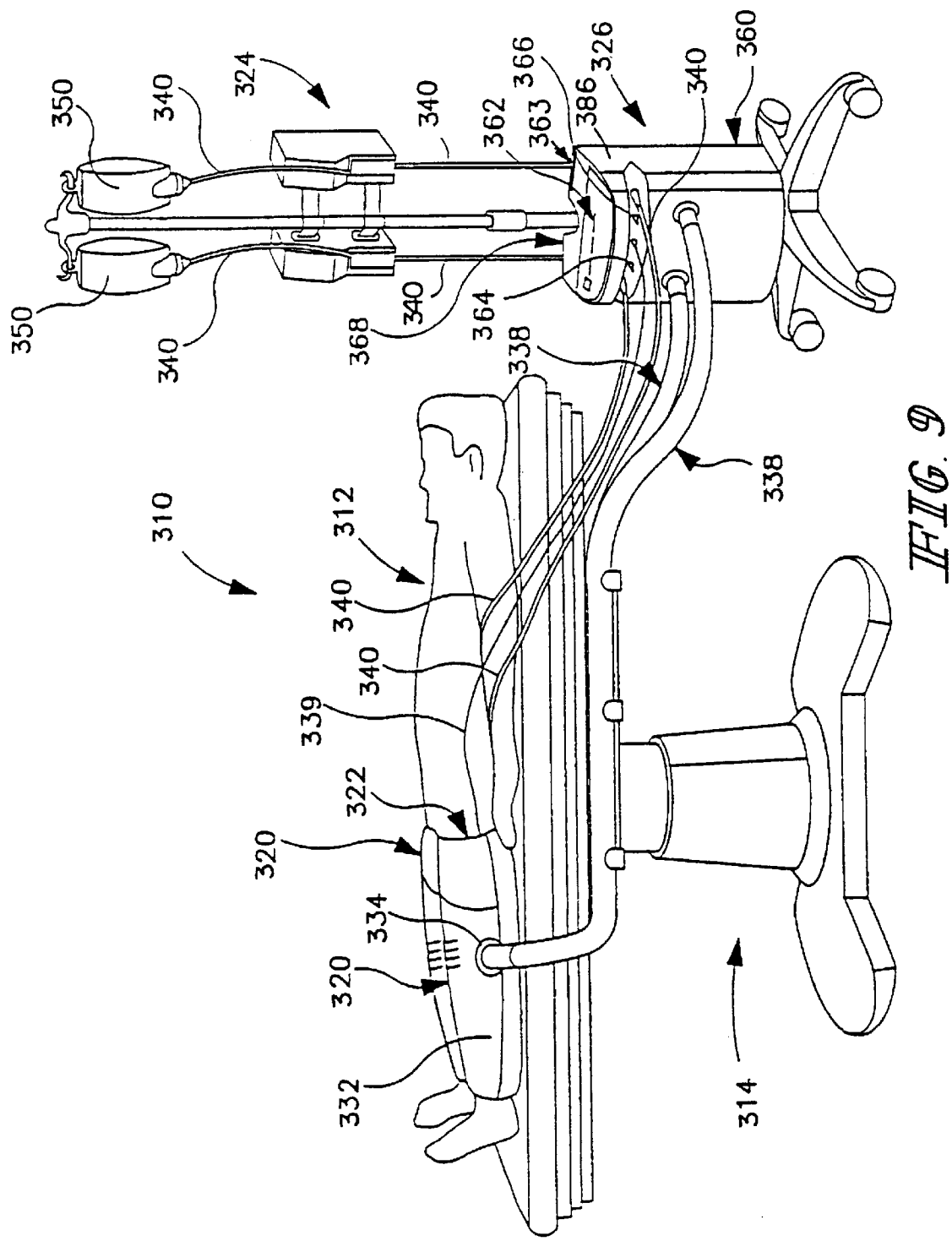
FIG. 9 is a perspective view of an illustrative system for regulating a core body temperature of a person in accordance with the present invention showing the system including a control apparatus mounted to a cart which also includes an intravenous supply system, a sleeve worn on each leg of the person, and a tube extending from each sleeve to the control apparatus to allow the control apparatus to control a flow of a medium through the tubes to the sleeves.

In another embodiment of the present invention, a regulation system 310 configured to regulate a core body temperature of a patient 312 lying on an operating room table 314 as shown in FIG. 9. The regulation system 310 includes a pressure applicator 320, a heating/cooling device 322, an intravenous device 324, and a control apparatus 326. The pressure applicator 320 is configured to apply either a negative pressure or a cyclical positive pressure to a portion (i.e., an extremity) of the patient 312 so that the blood vessels in the extremity vasodilate to promote heat absorption and transfer from the extremity to the patient's core body. The heating/cooling device 322 is then used to provide regulated heating or cooling to the extremity of the patient 312 so that the core body temperature of the patient 312 is controlled. The intravenous device 324 prevents a reduction in the core body temperature of patient 312 by permitting a pre-warmed intravenous solution 350 to be injected into the blood vessels of the patient 312. The control apparatus 326 controls the pressure applicator 320, heating/cooling device 322, and intravenous device 324 to regulate the core body temperature of the patient 312 as described below.

As shown in FIG. 9, pressure applicator 320 is preferably a sleeve that is configured to slide over an extremity of patient 312 such as any part of a leg or arm including the hands and the feet. (Note: two sleeves 320 are shown in FIG. 9, one sleeve 20 for each leg.) The sleeve 20 is configured to receive a medium (not shown) from a pressure generator 386 contained within control apparatus 326 so that a pressure, either negative or cyclical positive, can be applied to the portion of patient 312 covered by sleeve 320. The sleeve 320 includes a shell portion 332 defining an interior region (not shown) and an inlet portion 334. Inlet portion 334 is configured to allow the medium to enter the interior region so that the shell portion 332 expands or contracts to apply the negative or cyclical positive pressure to the portion of patient 312 enclosed by sleeve 320.

Heating/cooling device 322 is configured to heat or cool the portion of patient 312 being vasodilated by pressure applicator 320. Preferably, the heating/cooling device 322 is a thermal material (such as Gorix™ material) positioned between the pressure applicator 320 and the portion of the patient 312 being cyclically compressed, as shown in FIG. 9. The thermal material 322 is illustratively a heating element having a conductive fabric that allows low-voltage electricity to pass through the fabric to change the temperature of the fabric. The low voltage electricity passing through the Gorix material 322 causes the fabric to heat up in a uniform manner proportionally with voltage being applied.

A wire 339 is used to supply low-voltage electricity from the control apparatus 326 to the thermal material 322, as shown in FIG. 9. As described below, the control apparatus 326 supplies the appropriate amount of electrical voltage through wire 339 to thermal material 322 so that an appropriate amount of heat is applied to the extremity of patient 312 for regulating the core body temperature of patient 312.

Figure 10:
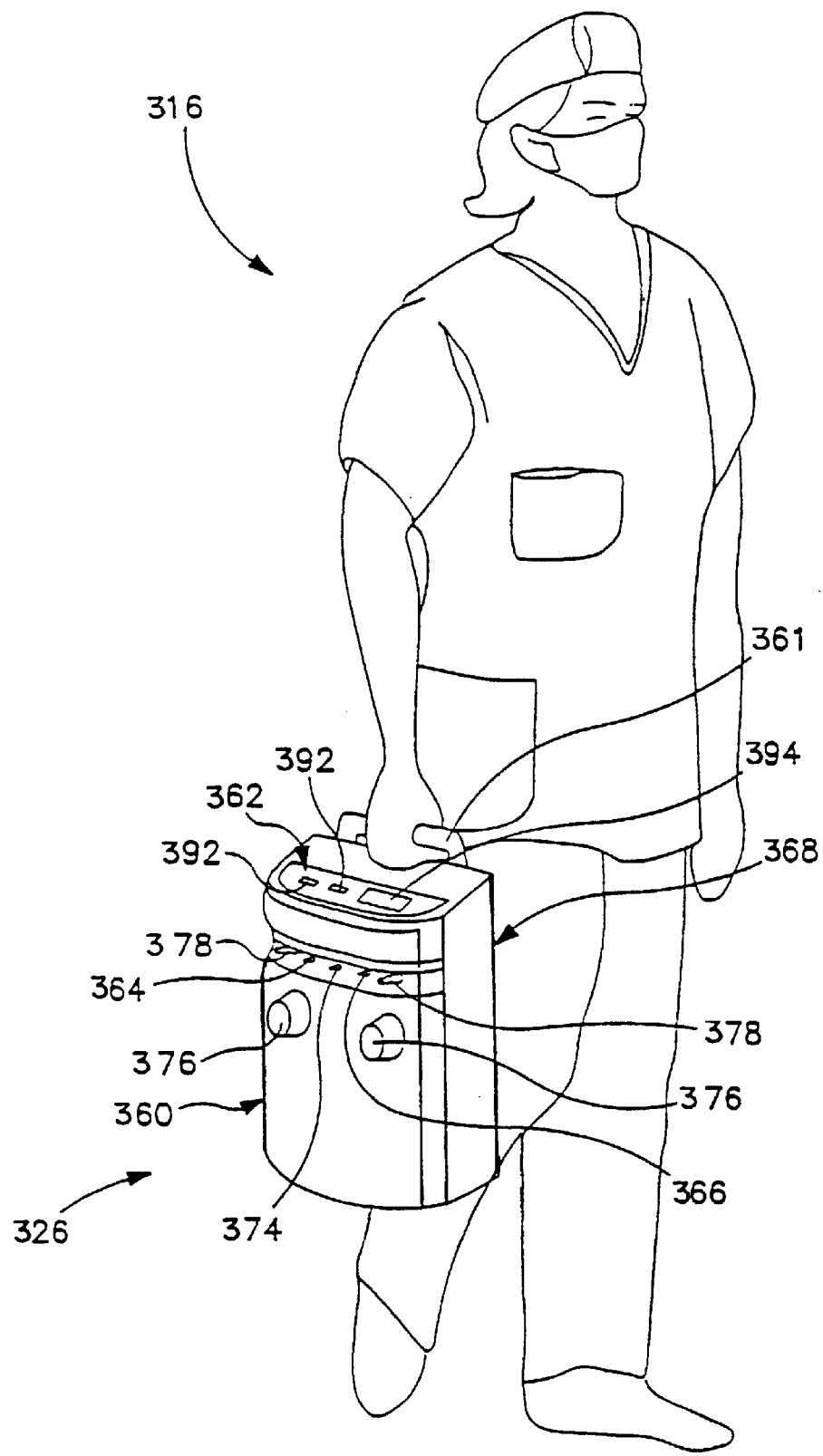
FIG. 10 is a perspective view of a nurse holding the control apparatus of FIG. 9 in one hand.

Control apparatus 326 is configured to control pressure applicator 320, heating/cooling device 322, and intravenous device 324 to regulate the core body temperature of patient 312 automatically. As shown in FIGS. 9 and 10, control apparatus 326 includes a housing 360, an input device 362 mounted to an outer surface of housing 360, a plurality of input ports 364, 366, 368, and a plurality of output ports 374, 376, 378. In addition, as shown in FIG. 3, control apparatus 326 includes a controller 384, a pressure generator 386, and an optional (as shown by the dotted lines) heating/cooling generator 388 contained within housing 360.

Housing 360, as shown in FIGS. 9 and 10, is formed to be box-shaped and includes a handle 361. Handle 361 allows control apparatus 326 to be carried by a caregiver 316 using one hand as shown in FIG. 10. In addition, the size and shape of box-shaped housing 360 allows control apparatus 326 to be easily moved from one location to another. The housing 360 may either be placed on the floor adjacent the table 314 or located on a cart as shown in FIG. 9.

Input device 362 is mounted to an outer surface of housing 360 of control apparatus 326. Input device 362 includes push buttons 392 and a display screen 394. Push buttons 392 allow caregiver 316 to input information into input device 362 which is then transferred to a controller. In addition, display screen 394 displays to caregiver 316 the status of various control functions and the values of the information input by caregiver 316 using push buttons 392. A caregiver 316 can input a reference temperature into input device 362 which is then transmitted to the controller. Reference temperature is then used by the controller to control heating/cooling device 322 and/or pressure applicator 320 to regulate the core body temperature of patient 312 as discussed below. It is understood that the input device 362 may be a separate input device which is either tethered to the housing 360 or a separate wireless remote control device. Further details of the regulation system 310 are described in PCT International Publication No. WO 99/23980 which is incorporated herein by reference.

Figure 11:
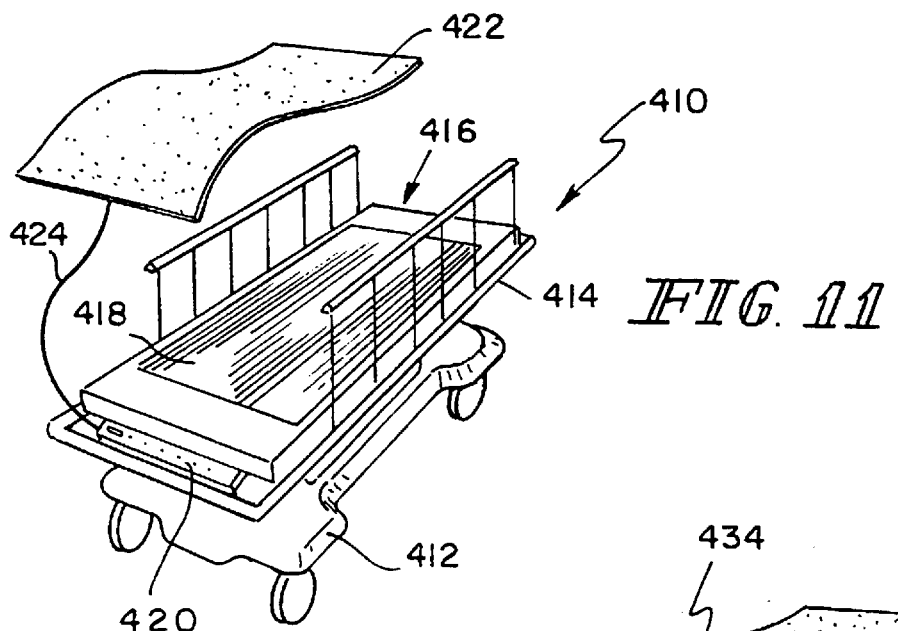
FIG. 11 is a perspective view of a stretcher with an integrated warming surface and a heated overlay.
Figure 12:
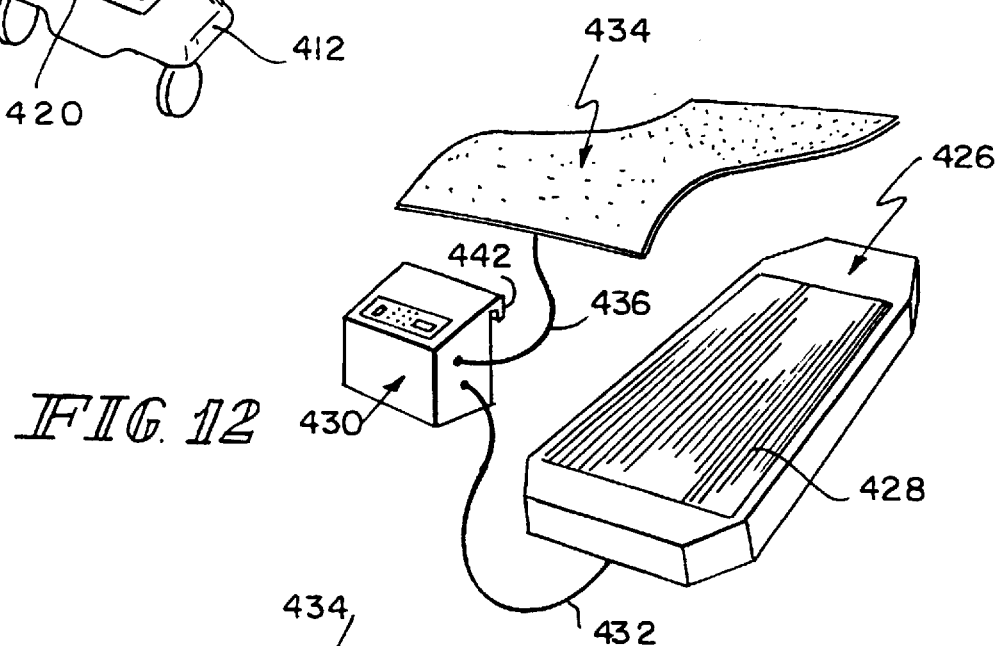
FIG. 12 illustrates a movable mattress having a warming surface and an optional overlay.
Figure 13:
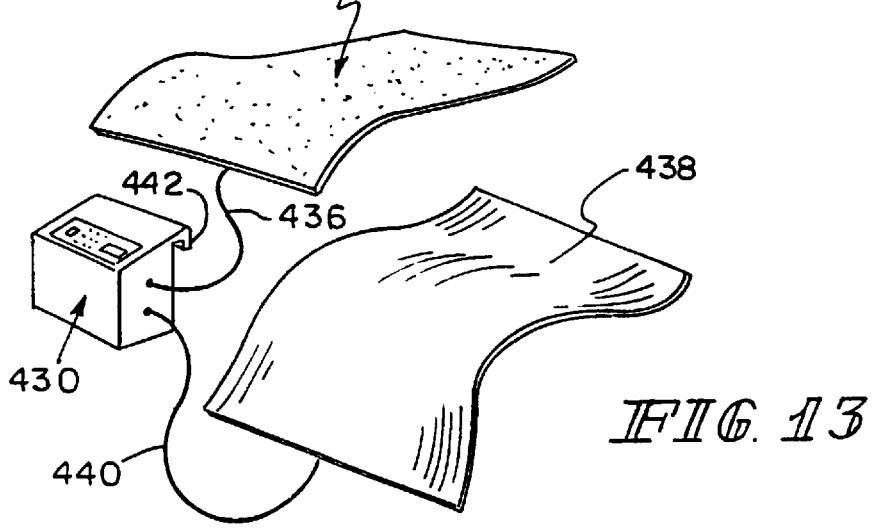
FIG. 13 illustrates first and second warming blankets coupled to a single controller.

Another embodiment of the present invention is illustrated in FIGS. 11–13. FIG. 11 illustrates a stretcher 410 having a base 412 and a frame 414 configured to support a mattress 416. Mattress 416 includes a resistive heating material warming pad 418 which is coupled to a controller 420 at an end of the frame 414. Therefore, the warming pad 418 is integrated with the mattress 416. An overlay blanket 420 including the resistive heating material is also coupled to the controller by line 424.

FIG. 12 illustrates a movable mattress 426 having an integrated warming pad 428 made of the resistive heating material. Warming pad 428 is coupled to controller 430 by line 432. An overlay blanket 434 is also coupled to controller 430 by a line 436. Therefore controller 430 controls both the integrated warming pad 428 and the warming blanket 434.

FIG. 13 illustrates the controller 430 coupled to two separate warming blankets 434 and 438. Blanket 438 is coupled to controller 430 by supply line 440. Therefore, one blanket 438 is located under a patient and the other blanket 434 is located over a patient. The controller 430 controls each of the blankets 434 and 438 to selected temperatures. Therefore, the warming blankets 434 and 438 can be moved to any stretcher or bed. Controller 430 includes a hook 432 to permit the controller 430 to be coupled to any stretcher or bed. In the embodiments of FIGS. 11–13, the warming pads can be placed over, under, or both over and under the patient.

The flexible conductive fabric such as Gorix material or another flexible conductive material is illustratively adhered between two layers of flexible waterproof ticking material such as Penn-Nyla Dartex. This provides a warming blanket that is able to contour around a patient to maximize body contact. The warming material covers the patient from the neck to the ankles and off the shoulders in width. Covering materials extend off the sides of the warming material and off the ends of the warming material so that the blanket can fully cover the patient on the sides and over the feet. This produces a full size blanket with a central heating zone for the core area of the patient.

Figure 14:
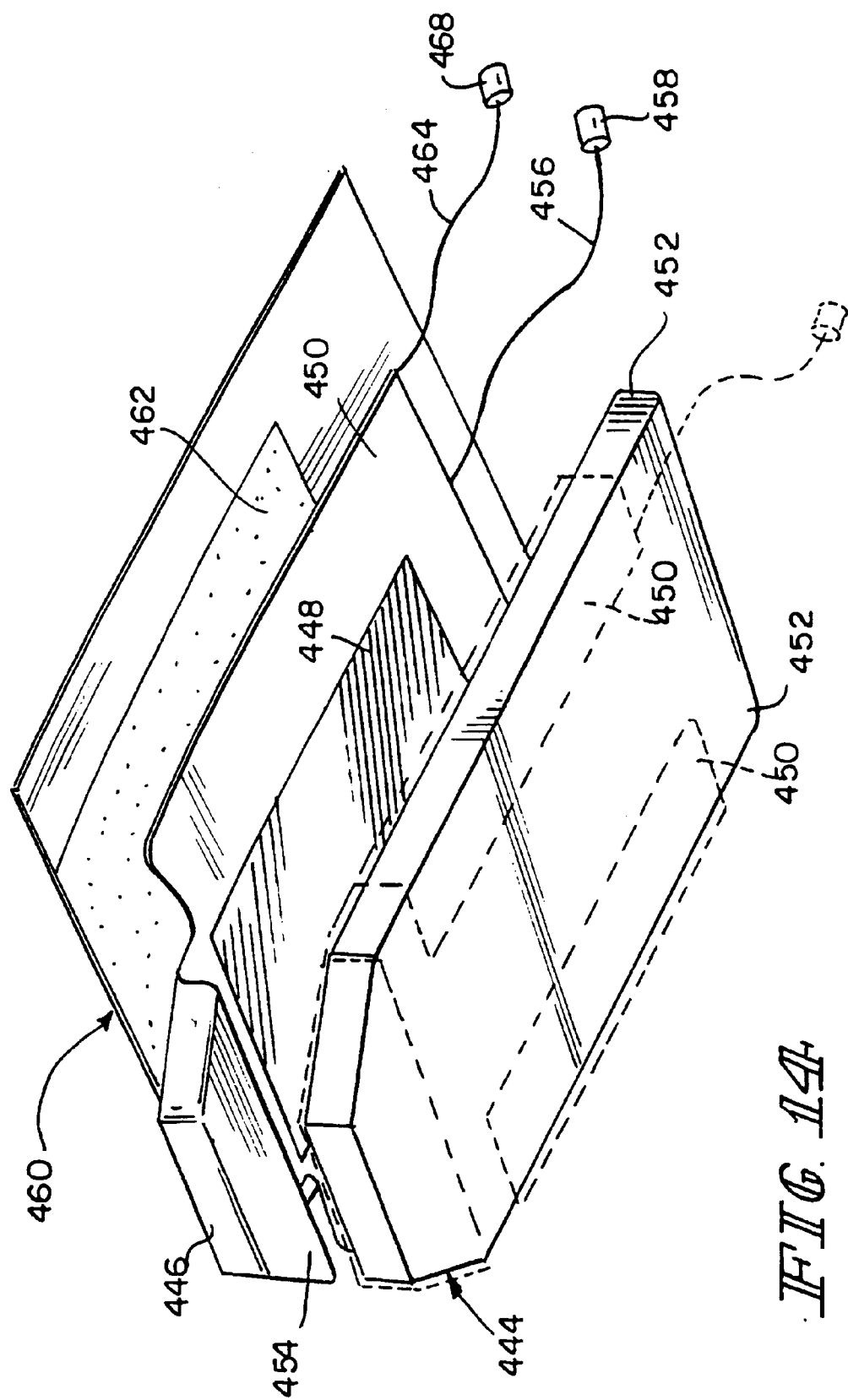
FIG. 14 is an exploded perspective view of a mattress topper having a heated warming surface and a warming blanket located above the warming surface.
Figure 13:
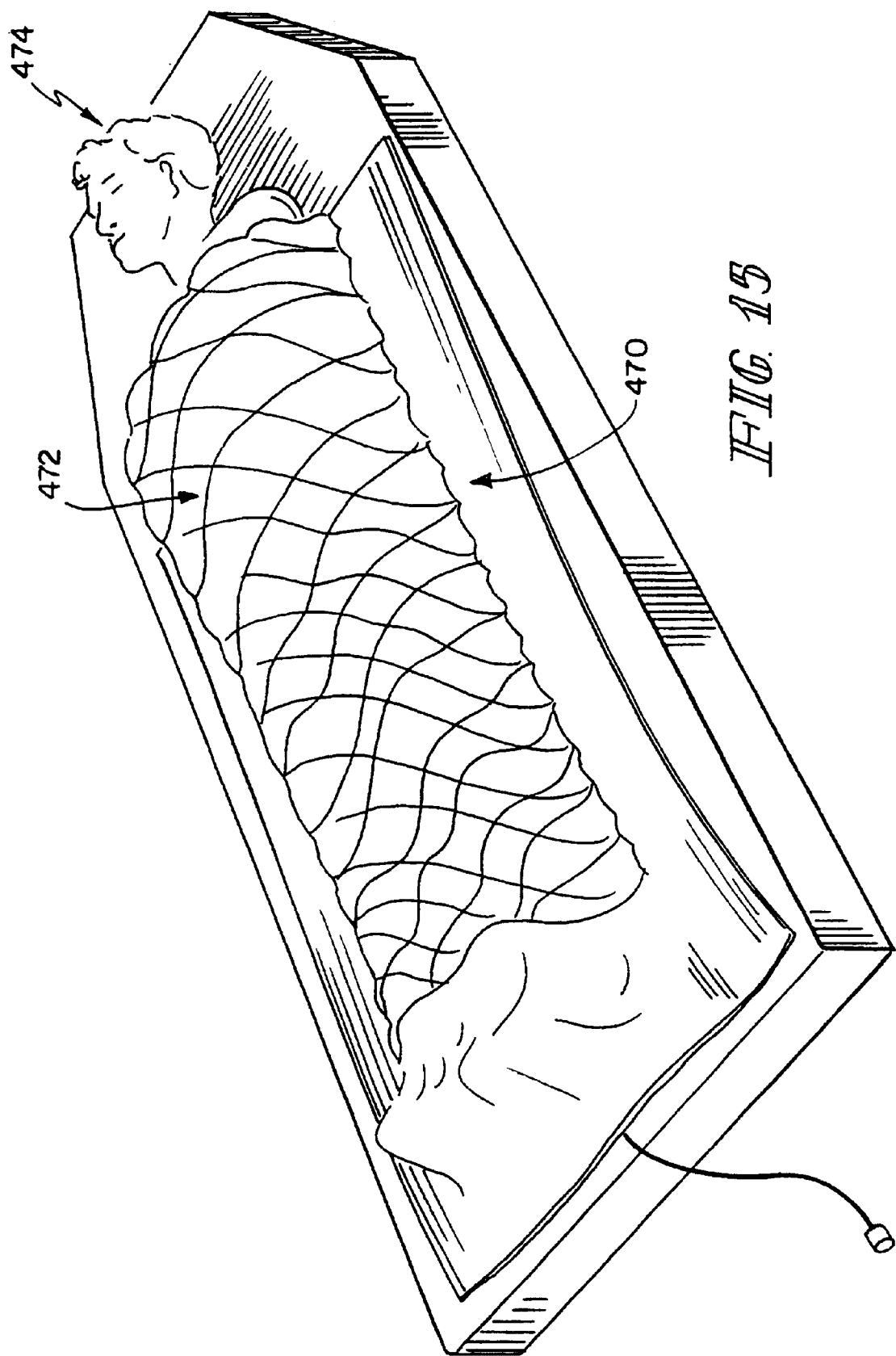

FIG. 14 illustrates a stretcher mattress 444 and an attachable warming surface 446 having a central warming pad 448 and side portions 450 configured to extend around side edges 452 of the mattress 444 so that the sides 450 can be tucked under the mattress 444 as shown in dotted lines in FIG. 14. Warming surface 446 includes a head end portion 454 which hooks over a head end of mattress 444. Therefore, warming pad 448 is located under the patient. A first line 456 and connector 458 are coupled to the warming pad 448. A warming blanket 460 is configured to be located over the patient. The warming blanket 460 includes a central heated portion 462 configured to be coupled to a controller by line 464 and connector 468. A single controller such as controller 430 is used to control both heating elements 448 and 462.

Another embodiment of warming blanket 470 is illustrated in FIG. 15. Blanket 470 includes a quilted area 472 which includes the resistive heating fabric of the present invention. The quilted portion 472 adds weight to the heating pad to help the warming material contact the skin surface of the patient 474.

Another warming blanket 476 is illustrated in FIG. 16. Warming blanket 476 includes a flexible outer area 478 which can be tucked in around the patient. Warming pad 476 is located within the quilted area 480. Illustratively, the quilting includes a polyester filler material 482 as shown in FIG. 17.

Figure 18:
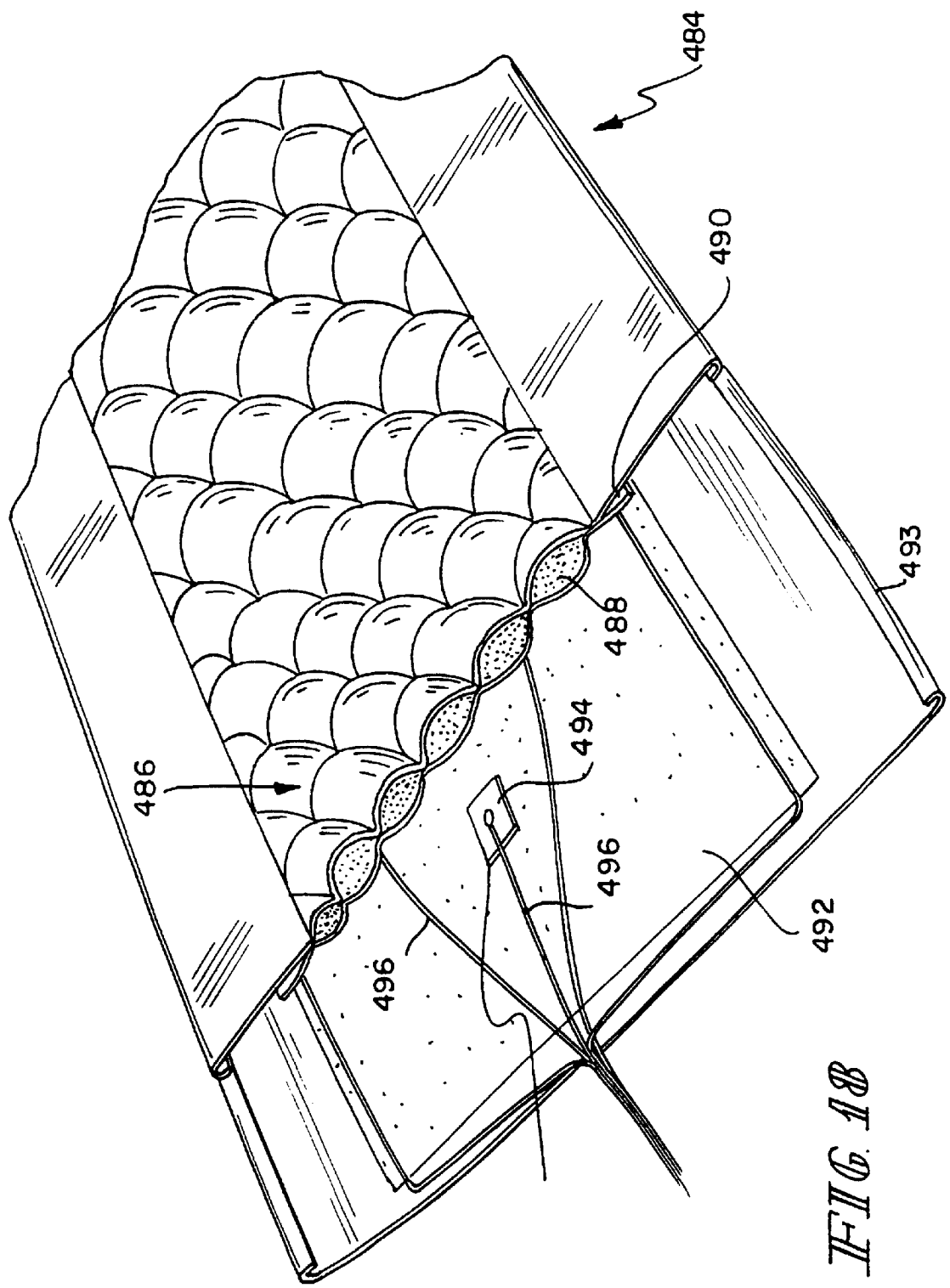
FIG. 18 is a perspective views illustrating further details of another warming blanket.

Another embodiment of the present invention is illustrated in FIG. 18. The warming blanket 484 includes a quilted topper 486 made from a weldable material such as two-sided Penn-Nyla. A polyester fiberfill material 488 is located in the quilted portion. A reflective layer 490 is coupled to the electroconductive fabric 492 at the edges. A bottom surface 493 is laminated to the thermally conductive pad. A reflective material 490 maximizes the heat transmitted down to the patient. The quilting on the warming blanket 484 provides a visual indication to the user where the heating area is located. The materials are illustratively welded together ultrasonically in a criss-cross quilted pattern. The top material corresponds in size to the overall blanket and the edges are bonded together to seal the entire unit.

Thermistors 494 are coupled to the warming surface 492 to control temperature. Illustratively, at least two thermistors 494 are used to measure temperature on different areas of the surface 492 to make sure the surface is heating evenly. Electrical leads 496 are coupled to the thermistors 494. Additional electrical leads extend down the sides of the heating element 492 to supply low voltage current to the heating material. The controller is illustratively a 110 VAC with a battery backup. The battery allows the caregiver to warm the patient during transport. The controller is illustratively sized to hang on an IV pole, or on a footboard or side rail of the bed. The controller can also be built into the bed or stretcher or on the footboard as discussed below.

FIG. 19 illustrates a stretcher 500 having a mattress 502 with a warming pad 504. The controller 506 is coupled to a frame 508 of the stretcher. As best shown in FIG. 20, the controller 506 rests on frame 508. Controller 506 is also located beneath a deck 510 of the stretcher 500.

FIG. 21 illustrates temperature controls 520 on a side rail 522 of a bed or stretcher. Bed articulation controls 523 are located adjacent controls 520. Illustratively, the controls 520 are connected to one or more heating pads on the patient support surface or on a blanket over the patient support surface. The controls 520 include an on/off button 524 along with an on/off indicator 526. In addition, a temperature down button 528 and a temperature up button 530 are provided for control by the patient. LEDs 532 indicate a temperature setting. The controller permits the patient to control the temperature of the heating elements within a preset maximum and minimum levels.

Another embodiment of the present invention is illustrated in FIG. 22. In this embodiment, a procedural recliner or chair 540 includes a seat section 542 and a back section 544. Seat section 542 includes a resistive heating pad fabric 546 and back section 544 includes a second resistive fabric heating pad 548. A controller 550 is built into the chair 540. Controller 550 controls both warming pads 546 and 548. An additional warming blanket 552 includes a warming area 554 made from the resistive fabric. Blanket 552 is also coupled to controller 550 by line 556. A controller 550 can either be plugged into a wall outlet, if available, or a battery backup on the chair 540 can be used for active warming of the patient during transport. Chair 540 may be used in a surgical setting. A control 560 is located on arm 562 of chair 540 to permit a patient to control temperature to a preset level set by the caregiver. Two buttons may be provided if desired to permit the temperature to be controlled within a predetermined range. Warming pads 546 and 548 may be integrated into cushions of the seat section 542 and back section 544. In addition, the warming pads 546 and 548 may fit over the top of existing chairs with flaps to couple the warming pads 546 and 548 to the various sections.

Although the invention has been described in detail with reference to a certain illustrated embodiments, variations and modifications exist within the scope and spirit of the invention as described and as defined in the following claims.

What is claimed is:

1. An apparatus for warming a patient, the apparatus comprising a patient support surface having an outer cover configured to contact the patient, a substantially continuous electrically conductive fabric located within the cover, and a controller electrically coupled to the conductive fabric to heat the electrically conductive fabric to a selected level.

2. The apparatus of claim 1, wherein the patient support surface is a mattress.

3. The apparatus of claim 1, wherein the patient support surface is a mattress on a stretcher.

4. The apparatus of claim 1, wherein the patient support surface is a mattress on a hospital bed.

5. The apparatus of claim 1, wherein the patient support surface is a mattress on a surgical table.

6. The apparatus of claim 1, wherein the patient support surface is on a patient transport backboard.

7. The apparatus of claim 1, wherein the patient support surface is a therapy device.

8. The apparatus of claim 7, wherein the therapy device is a pressure applicator configured to apply a pressure to a portion of the patient to promote heat absorption and transfer to the patient's core body.

9. The apparatus of claim 1, wherein the patient support surface is a seat cushion on a chair.

10. The apparatus of claim 1, wherein the patient support surface is a back cushion on a chair.

11. The apparatus of claim 1, further comprising a blanket having a second outer cover configured to contact the patient and a second electrically conductive fabric located within the second cover, the second electrically conductive fabric also being coupled to the controller so that the controller controls the temperature of both the first and second electrically conductive fabrics.

12. The apparatus of claim 1, wherein the controller is integrated into a siderail of a patient support apparatus.

13. The apparatus of claim 12, wherein the controller includes an on/off switch and temperature up/down switches for actuation by the patient.

14. The apparatus of claim 1, wherein the controller is a hand held controller.

15. The apparatus of claim 1, wherein the controller is a remote control device.

16. The apparatus of claim 1, wherein the controller includes a mounting portion.

17. The apparatus of claim 1, wherein the controller is integrated into a footboard of a patient support apparatus.

18. The apparatus of claim 1, wherein the electrically conductive fabric is coupled to a surface of an inner compartment which is filled with a plurality of beads.

19. The apparatus of claim 18, wherein the outer cover is made from a controlled air leakage material which holds its shape for a predetermined amount of time.

20. The apparatus of claim 1, wherein the electrically conductive fabric is located within a quilted section of the cover.

21. The apparatus of claim 20, wherein the quilted section is filled with a filler material.

22. The apparatus of claim 1, further comprising a reflective material located within the cover on an opposite side of the electrically conductive fabric from the patient.

23. The apparatus of claim 1, further comprising at least one thermistor coupled to the electrically conductive fabric, the at least one thermistor also being coupled to the controller.

24. The apparatus of claim 1, further comprising a plurality of air bladders located within the outer cover below the electrically conductive fabric.

25. The apparatus of claim 24, wherein the plurality of air bladders are selectively inflated and deflated to adjust a position of the patient.

26. The apparatus of claim 24 further comprising a foam base located below the plurality of air bladders located within the outer cover.

27. An apparatus for warming a patient, the apparatus comprising a movable patient support surface having an outer cover configured to contact the patient, an electrically conductive fabric located within the cover, and a controller electrically coupled to the conductive fabric to heat the electrically conductive fabric to a selected level while the patient support surface is being moved from one location to another.

28. The apparatus of claim 27, wherein the patient support surface is located on a patient support apparatus having a plurality of casters.

29. The apparatus of claim 27, wherein the patient support surface is on a patient transport backboard.

30. The apparatus of claim 27, further comprising a second cover separate from the outer cover of the patient support surface, and a second electrically conductive fabric located within the second cover, the controller being electrically coupled to the second conductive fabric so that the controller controls the temperature of both the first and second conductive fabrics.

31. An apparatus for warming a patient, the apparatus comprising a therapy device having a patient support surface configured to contact the patient, an electrically conductive fabric located adjacent the patient support surface, and a controller electrically coupled to the conductive fabric to heat the electrically conductive fabric to a selected level.

32. The apparatus of claim 31, wherein the therapy device is a pressure applicator configured to apply a pressure to a portion of the patient to promote heat absorption and transfer to the patient's core body.

33. An apparatus for warming a patient, the apparatus comprising a chair having a patient support surface configured to contact the patient, an electrically conductive fabric located adjacent the patient support surface, and a controller electrically coupled to the conductive fabric to heat the electrically conductive fabric to a selected level.

34. The apparatus of claim 33, wherein the patient support surface is one of a seat cushion and a back cushion of the chair.

35. The apparatus of claim 33, further comprising a cover separate from the patient support surface, and a second electrically conductive fabric located within the second cover, the controller being electrically coupled to the second conductive fabric so that the controller controls the temperature of both the first and second conductive fabrics.

36. An apparatus for warming a patient, the apparatus comprising a patient support surface, a first cover disposed adjacent the patient support surface and configured to contact the patient, a second cover configured to contact the patient, a first electrically conductive fabric located within the first cover, a second electrically conductive fabric located within the second cover, and a controller electrically coupled to the first and second conductive fabrics to control the temperature of the first and second conductive fabrics.

37. The apparatus of claim 36, wherein the patient support surface includes the first cover.

38. The apparatus of claim 36, wherein the second cover is separate from the patient support surface.

39. An apparatus for warming a patient, the apparatus comprising a patient support apparatus including a patient support surface including an outer cover configured to contact the patient and a barrier extending above the patient support surface, an electrically conductive fabric located within the outer cover, and a controller electrically coupled to the conductive fabric to heat the electrically conductive fabric to a selected level, the controller being integrated into the barrier of the patient support apparatus.

40. The apparatus of claim 39, wherein the controller includes an on/off switch and temperature up/down switches for actuation by the patient.

41. The apparatus of claim 39, wherein the controller includes a remote control device.

42. The apparatus of claim 39, wherein the barrier is a siderail of the patient support apparatus.

43. The apparatus of claim 39, wherein the barrier is one of a headboard and a footboard of the patient support apparatus.

44. The apparatus of claim 39, further comprising a second cover separate from the outer cover of the patient support surface, and a second electrically conductive fabric located within the second cover, the controller being electrically coupled to the second conductive fabric so that the controller controls the temperature of both the first and second conductive fabrics.

45. An apparatus for warming a patient, the apparatus comprising a patient support surface having an outer cover configured to contact the patient and an inner compartment which is substantially filled with a plurality of beads, an electrically conductive fabric coupled to a surface defining a portion of the inner compartment, and a controller electrically coupled to the conductive fabric to heat the electrically conductive fabric to a selected level.

46. The apparatus of claim 45, wherein the outer cover is made from a controlled air leakage material which holds its shape for a predetermined amount of time.

47. An apparatus for warming a patient, the apparatus comprising an outer cover having a surface configured to contact the patient, an electrically conductive fabric located within the cover, a controller electrically coupled to the conductive fabric to heat the electrically conductive fabric to a selected level, and a reflective material located within the cover on an opposite side of the electrically conductive fabric from the surface of the cover which contacts the patient.

48. The apparatus of claim 47, further comprising a quilted section of the cover located on an opposite side of the reflective material from the conductive fabric, the quilted section being filled with a filler material.

49. The apparatus of claim 47, further comprising at least one thermistor coupled to the electrically conductive fabric, the at least one thermistor also being coupled to the controller.

50. An apparatus for warming a patient, the apparatus comprising a patient support surface having an outer cover including a top surface configured to contact the patient, an electrically conductive fabric located within the cover, a controller electrically coupled to the conductive fabric to heat the electrically conductive fabric to a selected level, and a plurality of air bladders located within the outer cover below the electrically conductive fabric.

51. The apparatus of claim 50, wherein the plurality of air bladders are selectively inflated and deflated to adjust a position of the patient.

52. The apparatus of claim 50, further comprising a foam base located below the plurality of air bladders located within the outer cover.

53. The apparatus of claim 50, further comprising a second cover separate from the outer cover of the patient support surface, and a second electrically conductive fabric located within the second cover, the controller being electrically coupled to the second conductive fabric so that the controller controls the temperature of both the first and second conductive fabrics.

* * * * *